United States Patent
Charton et al.

(10) Patent No.: US 10,363,212 B2
(45) Date of Patent: Jul. 30, 2019

(54) AESCULUS HIPPOCASTANUM EXTRACT

(71) Applicant: Gattefossé SAS, Saint-Priest (FR)

(72) Inventors: Virginie Charton, Genas (FR); Benoît Caprin, Lyons (FR); Nicolas Bechetoille, Brignais (FR)

(73) Assignee: Gattefossé SAS, Saint-Priest (FR)

( * ) Notice: Subject to any disclaimer, the term of this patent is extended or adjusted under 35 U.S.C. 154(b) by 18 days.

(21) Appl. No.: 15/642,336

(22) Filed: Jul. 6, 2017

(65) Prior Publication Data
US 2018/0015027 A1   Jan. 18, 2018

(30) Foreign Application Priority Data

Jul. 13, 2016  (FR) .................................... 16 56736

(51) Int. Cl.
| | | |
|---|---|---|
| *A61K 36/77* | (2006.01) | |
| *A61K 8/97* | (2017.01) | |
| *A61K 8/04* | (2006.01) | |
| *A61K 8/06* | (2006.01) | |
| *A61Q 19/00* | (2006.01) | |
| *A61Q 19/08* | (2006.01) | |

(52) U.S. Cl.
CPC ................ *A61K 8/97* (2013.01); *A61K 8/042* (2013.01); *A61K 8/064* (2013.01); *A61Q 19/00* (2013.01); *A61Q 19/08* (2013.01); *A61K 2800/78* (2013.01)

(58) Field of Classification Search
None
See application file for complete search history.

(56) References Cited

U.S. PATENT DOCUMENTS

| | | | | |
|---|---|---|---|---|
| 5,391,373 A | * | 2/1995 | Mausner | A61K 8/365 424/401 |
| 2005/0048008 A1 | * | 3/2005 | Gupta | A61K 8/447 424/59 |
| 2010/0331272 A1 | * | 12/2010 | Kameyama | A61K 8/63 514/33 |

FOREIGN PATENT DOCUMENTS

| | | |
|---|---|---|
| DE | 1194529 | 6/1965 |
| FR | 1422009 | 12/1965 |
| WO | WO 2009/107853 | 9/2009 |

OTHER PUBLICATIONS

Barreira J. et al. Antioxidant Activities of the Extracts from Chestnut Flower, Leaf, Skins, and Fruit. Food Chemistry 107(3)1106-1113, Apr. 2008. (Year: 2008).*
Chen J. et al. Determination of Four Major Saponins in the Seeds of Aesculus chinensis Bunge . . . Analytica Chimica Acta 596:272-280, 2007. (Year: 2007).*
Patlolla J. et al. Anti-Inflammatory and Anti-Cancer Properties of Beta Escin, a Triterpene Saponin. Current Pharmacology Rep 1: 170-178, 2015. (Year: 2015).*
Milczarek D. Horse Chestnut Triterpenes. J of the Polish Society of Cosmetic Chemists 1:36-39, 2010. (Year: 2010).*
Search Report and Written Opinion [Rapport de Recherche Préliminaire et Opinion Ecrite] dated Nov. 11, 2016 From the Institut National de la Propriété Industrielle de la République Française, INPI Re. Application No. FR1656736. (6 Pages).
Mintel "Protect Barrier Rich", Database GNPD [Online], XP002764077, Database Accession No. 3967717, May 31, 2016.

* cited by examiner

*Primary Examiner* — Ralph J Gitomer

(57) ABSTRACT

An *Aesculus hippocastanum* extract able to be obtained by an extraction method comprising a solid/liquid extraction step of the flower, followed by a second solid/liquid separation step, and lastly a third step for recovering the liquid phase, characterized in that the solvent consists of a mixture of fructose and glycerin optionally comprising water.

6 Claims, No Drawings

AESCULUS HIPPOCASTANUM EXTRACT

RELATED APPLICATION

This application claims the benefit of priority of French Patent Application No. 1656736 filed Jul. 13, 2016, the contents of which are incorporated herein by reference in their entirety.

FIELD AND BACKGROUND OF THE INVENTION

The invention relates to a horse chestnut, or *Aesculus hippocastanum*, extract. It also relates to a cosmetic composition comprising said extract. It lastly relates to the use of the extract for the cosmetic treatment of the skin and/or mucosa.

The horse chestnut tree (*Aesculus hippocastanum*) is a large tree reaching up to 30 m tall; it grows quickly, has a robust and straight trunk, and is ball-shaped. The reddish-brown bark stays smooth for a long time, then cracks lengthwise, peels, and detaches in plaques. Its foliage is deciduous. The pointy buds appear in the fall and are protected by a very sticky resin. The leaves are opposite, palmate and large (30 to 50 cm). The inflorescence is made up of white zygomorphic flowers, often with red or yellow spots. The fruit is a green capsule (chestnut husk) with a thick, smooth wall that contains one (sometimes two or three) large, smooth and glossy brown seed(s), known as "chestnut". This seed is not edible.

The horse chestnut tree is a particularly widely used plant species in cosmetics, dermocosmetics and the pharmaceutical industry.

The use of horse chestnut seed extracts, primarily containing a mixture of triterpene saponins known as aescin (or escin), is known in the prior art in many preparations to treat chronic venous insufficiencies and to relieve certain symptoms, such as heavy and swollen legs. Aescin reduces capillary fragility by inhibiting the hyaluronidase enzyme. Aescin also has anti-inflammatory, antineoplastic, neuroprotective and antioxidant properties. Although many cosmetic preparations include *Aesculus hippocastanum* seed extracts for their effects on blood circulation, other beneficial effects for the skin are attributed to it as well. An *Aesculus hippocastanum* seed extract has antioxidant properties greater than those of ascorbic acid and protects the cells from oxidative stress. An *Aesculus hippocastanum* seed extract causes fibroblast contraction and decreases wrinkles around the eye contours. Document WO2009/107853 A2 for example describes an agent comprising a triterpene saponin obtained by ethanol-water extraction of the *Aesculus hippocastanum* seeds, which stimulates the contraction of the dermal fibroblasts to prevent and improve wrinkles and skin slackening with age. *Aesculus hippocastanum* seed extracts improve the protective performance of sun filters. Document WO2009/107853 A2 describes a saponin-rich *Aesculus hippocastanum* seed extract for an anti-aging effect. This extract is obtained using an alcoholic solvent.

The use of horse chestnut bark extracts is also known in the prior art. Its bark, which has astringent properties, is used to combat diarrhea when taken orally and for antiseptic purposes when applied locally on wounds and ulcers. The bark extracts primarily contain coumarins, such as esculin (or aesculin, or esculoside), fraxin, esculetin and fraxetin, as well as tannins, considered to be vasoprotective and in particular used to treat hemorrhoids, edema.

Document US 2005/048008 A1 describes cosmetic compositions to treat skin aging and to improve skin appearance. This document describes an *Aesculus hippocastanum* extract, but without specifying the part of the plant from which the extract is obtained. Furthermore, nothing is indicated regarding the nature of the solvent used.

The use of *Aesculus hippocastanum* flower extract is described in traditional medicine for internal or external use, to treat venous inflammation, varicose veins, hemorrhoids and frostbite. The flower contains flavonoids, and primarily glycosylated derivatives of kaempferol and quercetin. The presence of derivatives of the tannin, coumarin, amine and amino acid type has also been reported. There is also a monograph recorded in the French Pharmacopeia for a homeopathic preparation from *Aesculus hippocastanum* flowers. In this case, it involves a mother tincture obtained by hydroethanolic extraction (45/55 V/V) of fresh flowers carried out using the general technique for preparing mother tinctures. The MINTEL document (database accession number 3967717) describes a cosmetic composition for treating the skin comprising an *Aesculus hippocastanum* flower extract. This document does not describe the nature of the solvent used to obtain the flower extract.

For a solvent polarity range comprised between that of ethanol and water, the presence of saponins and/or coumarins may cause a potential toxicity of the extracts, notwithstanding their aforementioned efficacy.

Furthermore, the choice to be made among the available solvents to obtain extracts raises a certain number of difficulties.

Aqueous solvents require the addition of a microbiological preservative to guarantee their stability. Yet the usage field of preservatives is increasingly restricted, in particular due to the required toxicological data. Propylene glycol has proven potentially toxic, and the current trend for manufacturers is to avoid it. Agro-sourced butylene glycol is relatively expensive, which limits its industrial use. Agro-sourced propanediol has the drawback of being derived from genetically modified corn (GMO), which is not readily accepted by consumers, and regarding which some reservations may be wise. Ethanol, although having good extraction power alone or mixed with water, is particularly volatile and flammable, which causes transport and storage problems. Furthermore, due to its drying nature, this solvent may disrupt the hydrolipidic film of the skin and cause irritation for sensitive skin.

Furthermore, plant extracts often being intended to be formulated in cosmetic compositions, it is important to avoid extraction solvents comprising salts or acids, at least trace amounts of which will necessarily be found in the extract. Indeed, it is well known in the prior art that the formulation, as a gel or emulsion, of salt-based ingredients beyond a dose of 0.1% is particularly complex. Furthermore, acids, by decreasing the pH of the obtained extracts, result in making gel or emulsion formulations difficult. In particular, cosmetic products for cutaneous application must have an appropriate pH, preferably close to that of the skin (approximately pH 6.5), or neutral. Under these conditions, the use of solvents containing acids therefore requires the addition of excipients, in particular pH regulators.

SUMMARY OF THE INVENTION

In other words, the problem the invention proposes to resolve is that of developing an *Aesculus hippocastanum* extract that does not have the aforementioned drawbacks, in particular that is free of coumarin, in particular aesculin, and free of saponins, in particular aescin.

Another problem that the invention proposes to resolve is that of developing an *Aesculus hippocastanum* extract that is free of toxic or irritant effects.

In parallel, there is a continuous search for solutions to improve skin appearance, or to prevent or decrease wrinkles, or more generally, skin slackening. One avenue being considered is that of stimulating the expression of collagen IV, collagen VII and fibronectin, these proteins all being involved in the dermal-epidermal junction (DEJ).

The DEJ is involved in several biological processes, such as tissue repair, attachment, migration, proliferation and epidermal differentiation. The DEJ is also a cytokine storage site, a growth factor reservoir, a selective filter for controlling the exchanges of cells, macromolecules and nutrients, and a chemical and physical barrier. This last function is particularly important, since it is through the DEJ that the cohesion between the epidermis and the dermis occurs, which allows resistance to external cutaneous pulling forces.

The DEJ is made up of hemidesmosomal proteins and an epidermal basement membrane, which is a complex and organized molecular network. The epidermal basement membrane is formed by three separate superimposed layers:
- the lamina lucida: fine anchoring filaments that are inserted in the lamina densa;
- the lamina densa: fine layer of highly specialized extracellular matrix resulting from the arrangement of the protein networks of type IV collagen and laminin, associated with fibronectin;
- the lamina reticularis: fibrous zone made up of anchoring fibrils, the main component of which is type VII collagen.

The aging process leads to significant modifications to the structure and composition of the DEJ. In particular, the proteolytic deterioration of the components of the basal membrane disrupts the structural organization of the DEJ, which, during aging, loses its viscoelastic properties. The composition of the DEJ also appears to vary greatly with age, the collagen IV and collagen VII being reduced.

Consequently, another problem that the invention proposes to resolve is that of developing a cosmetic composition that has interesting properties to stimulate the synthesis of the proteins of the DEJ, in particular collagen IV, collagen VII and fibronectin.

The Applicant has resolved all of these problems by developing an *Aesculus hippocastanum* extract able to be obtained using an extraction method comprising a solid/liquid extraction step of at least part of the plant, followed by a second solid/liquid separation step, and lastly a third step for recovering the liquid phase.

The invention is characterized in that the solvent consists of a mixture of fructose and glycerin, optionally comprising water.

The extract according to the invention is free of saponin and coumarin. It is primarily made up of flavonoids, catechic derivatives and amino acids.

Advantageously, the extract has a flavonoid content level comprised between 10 and 200 mg/100 g of extract, advantageously between 50, preferably 75, and 100 mg/100 g of extract.

Likewise, the extract has a free amino acid content level comprised between 10 and 200 mg/100 g of extracts, advantageously between 50, preferably 75, and 100 mg/100 g of extract.

The extract according to the invention is therefore particularly interesting because it is free of components likely to irritate the skin or the mucosa. The cosmetic compositions comprising it are therefore also less likely to create cutaneous reactions.

Furthermore, the solvent developed by the Applicant is free of organic acids, inorganic compounds and salts. Additionally, this solvent is free of glycol, alcohol, mineral salts, and acids. Thus, its chemical composition does not hinder formulation as a gel or an emulsion.

Consequently, the extract obtained with this solvent, and which necessarily comprises trace amounts of the extraction solvent, has the same advantages and is particularly suitable for the formulation of cosmetic products.

According to a first feature, the solvent may or may not contain water. The presence of water in the solvent nevertheless has the advantage of fluidifying the solvent, and thus facilitating the extraction. In other words and in a first advantageous embodiment, the solvent consists of a mixture of fructose, glycerin and water.

Furthermore, when the components of this solvent are present in certain molar ratios, the solvent has the properties of a NADES solvent, i.e., a eutectic solvent made up of molecules found in nature, and bonded together through intermolecular interactions, in particular hydrogen bonds. The solvent is in particular liquid at ambient temperature, which facilitates the implementation of the method leading to the extract according to the invention.

In one particular embodiment, the solvent consists of a mixture of fructose, glycerin and water in molar proportions comprised between 1:1:3 and 1:1:7, preferably in molar proportions of about 1:1:5.

In practice, the solvent used can be produced by mixing fructose and glycerin, or fructose, glycerin and water, in an agitated reactor, until a colorless, clear mixture is obtained. This mixture can be obtained at a temperature comprised between 2° C. and 100° C. and for 0.5 to 6 hours, preferably 40° C. to 70° C. for 1 to 2 hours.

According to the invention, all or part of the *Aesculus hippocastanum* plant can be implemented in the method according to the invention. In practice, the part of the plant implemented in the method is chosen from the group comprising the flower, the seed, the leaf.

Particularly preferably, the part of the plant implemented is the flower. This may be a fresh, frozen, dried flower, whole, cut or ground. Advantageously, it is a dry and ground flower.

The extract according to the invention can be obtained using a method implementing a solid/liquid extraction step.

The solid/liquid extraction can be carried out using various techniques well known by those skilled in the art, such as maceration, remaceration, digestion, dynamic maceration, decoction, fluid bed extraction, microwave-assisted extraction, ultrasound-assisted extraction, counter-current extraction, percolation, re-percolation, leaching, extraction under reduced pressure, diacolation.

In practice, the plant/solvent weight ratio applied for the extraction step is comprised between 1/99 and 10/90. The extraction step is preferably carried out at a temperature comprised between 2 and 100° C., more preferably between 20 and 80° C. The extraction step can be maintained for several minutes to several days.

In order to optimize the extraction of the active ingredients while protecting these compounds from oxidation by the oxygen in the air, the solid/liquid extraction step is advantageously carried out under agitation and/or under a nitrogen atmosphere.

According to the invention, the solid/liquid extraction step is followed by a solid/liquid separation step, the goal being to recover the liquid phase, also known as solid/liquid separation filtrate, containing the active ingredient. This separation can be carried out using any technique known by those skilled in the art, in particular draining, pressing, wiping, centrifugation or filtration.

Optionally, the liquid/solid separation step can be followed by a concentration step, which makes it possible to obtain a concentrate, in liquid or semisolid form depending on the concentration factor. In practice, the concentration step can be carried out by evaporation under reduced pressure or reverse osmosis.

Preferably, the solid/liquid separation filtrate or the concentrate further undergo one or several clarification steps. To carry out this clarification step, one skilled in the art may use any type of filtration known in the art in question.

Lastly, for packaging, the method making it possible to obtain an extract according to the invention can comprise a sterilizing filtration. The sterilizing filtration is traditionally carried out by filtering the product through a filter comprising pores with a diameter of about 0.22 µm. Preferably, the sterilizing filtration step is the final step of the method.

The Applicant has further discovered that the extract according to the invention has particularly interesting biological properties, in particular on the stimulation of protein synthesis of the skin, these properties not being obtained with *Aesculus hippocastanum* extracts obtained using the traditional hydroethanolic extraction approach.

Indeed and as outlined in the experimental section, the extract according to the invention in particular has the property of stimulating the expression of collagen IV, collagen VII and fibronectin, these proteins all being involved in the DEJ.

The extract according to the invention, stimulating the synthesis of collagen IV, collagen VII and fibronectin, is therefore particularly interesting for cosmetic uses, in particular seeking to improve skin appearance, or to prevent or decrease wrinkles and skin slackening, and more generally for the cosmetic treatment of the skin and mucosa.

The invention therefore also relates to the use, preferably non-therapeutic, of the extract according to the invention or compositions comprising it, for the cosmetic treatment of the skin and/or mucosa, in particular to improve the appearance of the skin and/or mucosa, to improve cutaneous strength and/or elasticity, to treat or prevent skin aging, wrinkles, or skin slackening.

From this perspective, the invention also relates to compositions comprising the inventive extract, preferably cosmetic compositions, i.e., suitable for topical application on the skin and/or mucosa, and/or keratinous appendages.

Preferably, in the composition according to the invention, the extract according to the invention represents between 0.1% and 10%, preferably between 0.5% and 5% by weight of the composition.

The composition according to the invention may assume all pharmaceutical forms normally used for topical application on the skin and/or the mucosa, and/or the keratinous appendages, for example in anhydrous form, in the form of an oil-in-water emulsion, a water-in-oil emulsion, a multiple emulsion, or a silicone emulsion, a micro-emulsion, a nanoemulsion, a gel, an aqueous solution or a hydro-alcoholic solution.

This composition may be more or less fluid and assume the form of a white or colored cream, a pomade, a milk, a lotion, a serum, or a gel.

The cosmetic and/or dermatological composition may contain the excipients typically used in the cosmetic and dermatological fields, such as fats, detergent and/or conditioning surfactants, emulsifiers and co-emulsifiers, hydrophilic or lipophilic gelling agents, preservatives, antioxidants, solvents, exfoliating agents, perfumes, fillers, hydrophilic and lipophilic filters, colorants, neutralizers, pro-penetration agents, and polymers. These types of excipients are all well known by those skilled in the art.

In practice, the quantities of these various excipients are those traditionally used in the fields in question, and the sum of the excipients preferably represents 0.01% to 30% of the total weight of the composition.

Appropriate fats include mineral oils, animal oils (such as lanolin), plant oils, synthetic oils (for example, isopropyl myristate, octyldodecyl, isostearyl isostearate, decyl oleate, isopropyl palmitate), silicone oils (cyclomethicone, dimethicone) and fluorinated oils. Fatty alcohols, fatty acids, waxes and gums, and in particular silicone elastomers, can be used as fats.

Appropriate detergent and/or conditioning surfactants include non-ionic, anionic, cationic or amphoteric surfactants, and mixtures thereof, for example aklylsulfates, alkylethersulfates, such as lauryl ether sodium sulfate, alkyl betaines, such as cocamidopropylbetaine, or quaternary ammonium salts.

Appropriate emulsifiers and co-emulsifiers for example include polyglycerol and fatty acid esters, sucrose and fatty acid esters, sorbitan and fatty acid esters, fatty acid and oxyethylene sorbitan esters, fatty acid and PEG ethers, glycerol and fatty acid esters, alkyl sulfates, alkyl ether sulfates, alkyl phosphates, alkyl polyglucosides, dimethicone copolyols.

Appropriate hydrophilic gelling agents for example include carboxyvinyl polymers (carbomers), acrylic copolymers, such as acrylate/alkylacrylate copolymers, polyacrylamides, polysaccharides, such as xanthan gum, guar gum, natural gums, such as cellulose gum, and derivatives, starches and derivatives thereof, clays and 2-acrylamido-2-methylpropane acid copolymers.

Appropriate lipophilic gelling agents for example include modified clays such as bentones, fatty acid metallic salts, hydrophobic silica and ethylcellulose.

Appropriate preservatives for example include benzoic, sorbic, propionic, salicylic, dehydroacetic acids and salts thereof, benzylicacid, ethylhexylglycerine, parabens, salts and esters thereof, triclosan, imidazolidinyl urea, 5 phenoxyethanol, DMDM hydantoin, diazolidinyl urea, chlorphenesin.

Appropriate antioxidants for example include chelating agents such as EDTA and salts thereof, sodium metabisulfite, salicylic, ascorbic and citric acids and salts thereof, sodium tartrate, sodium gluconate, carotenoids and tocopherols.

Solvents usable in the cosmetic composition (separate from the extraction solvent) include water, ethanol, glycerin, propylene glycol, propanediol, butylene glycol, sorbitol.

Appropriate exfoliating agents for example include chemical exfoliators such as AHAs, physical exfoliators such as natural or synthetic powders.

Appropriate fillers for example include talc, kaolin, mica, serecite, magnesium carbonate, aluminum silicate, magnesium silicate, organic powders, such as nylon.

Appropriate filters for example include UVA and UVB filters traditionally used, such as benzophenone-3, butyl methoxydibenzoyl methane, octocrylene, octyl methoxycinnamate, 4-methylbenzylidene camphor, octyl salycylate, tacephthalydene dicamphor sulfanic acid, drometrizole trisiloxane, methylene bis benzotriazolyl tetramethylbutylphenol, bis-ethylhexyloxyphenol methoxyphenyl triazine, ethylhexyl triazone, and Diethylamino Hydroxybenzoyl Hexyl Benzoate. $TiO_2$ and ZnO filters are also cited in their micrometric and nanometric forms, coated and non-coated.

Appropriate colorants for example include lipophilic colorants, hydrophilic colorants, pigments and nacres typically used in cosmetic or dermatological compositions, and mixtures thereof.

Appropriate neutralizing agents for example include sodium hydroxide, triethanolamine, aminomethyl propanol, potassium hydroxide.

Appropriate pro-penetration agents for example include alcohols and glycols (ethanol, propylene glycol), ethoxydiglycol, alcohols and fatty acids (oleic acid), fatty acid esters, dimethyl isosorbide.

The composition according to the invention may also further contain active ingredients other than the extract according to the invention. Appropriate active ingredients for example include anti-radicals, or more generally, anti-oxidants, whiteners, pigments, emollients, moisturizers, anti-seborrheics, anti-inflammatories, anti-acne agents, keratolytic and/or peeling agents, anti-wrinkle and tensor agents, draining agents, anti-irritation agents, soothing agents, vitamins and mixtures thereof, matting agents, anti-aging agents such as retinal, healing agents, antiseptics and essential oils.

DESCRIPTION OF SPECIFIC EMBODIMENTS OF THE INVENTION

The invention and resulting benefits will become clear from the following exemplary embodiments.

EXAMPLES

Example 1

Manufacture of *Aesculus hippocastanum* Extracts

One mixes 1 part dried and ground flowers or ground seeds of *Aesculus hippocastanum* and 19 parts of a 70:30 weight/weight ethanol/water mixture (denoted EtOH/Water solvent) or a Fructose/Glycerin/Water mixture in molar ratio 1:1:5 (denoted FGW solvent). The mixture is extracted at 70° C. for 3 h, then the extract is filtered. One thus obtains a clear, brown-yellow hydroethanolic flower extract (denoted EtOH/water flower extract) and a clear amber Fructose/Glycerin/Water flower extract (denoted FGW flower extract). Lastly, one obtains a hydroethanolic seed extract (denoted EtOH/water seed extract) and a Fructose/Glycerin/Water seed extract (denoted FGW seed extract), both of which are clear and light yellow.

Example 2

Characterization of the Composition in Free Amino Acids in the *Aesculus hippocastanum* Extracts The content levels of free amino acids contained in the extracts obtained in example 1 are quantified by HPLC (Shimadzu R_LCS_01) on a Waters Novapack C18 column. The FGW extract is derived after dilution at 1/5 in (w/V) in water. The hydroethanolic extracts are diluted at 1/2 (volume/volume) in water, filtered at 0.45 µm, then derived. The calibration is performed externally with the assay kit. The obtained results are provided in Table 1 below.

TABLE 1

| Free amino acid content levels | | | |
|---|---|---|---|
| Solvent | FGW | EtOH/water | EtOH/water |
| Part used | Flower | Flower | Seed |
| Free amino acid level (in mg/100 g) | 89.0 | 76.7 | 7.2 |

Conclusion:

The FGW flower extract is significantly richer in free amino acids than the EtOH/water flower extract. The very low free amino acid content level of the EtOH/water extract proves that the chemical composition of the flowers and the seeds is significantly different. The flower extracts and the seed extracts of *Aesculus hippocastanum* clearly have a different composition.

Example 3

Search for the Presence of Saponins and Coumarins in the *Aesculus hippocastanum* Flower Extracts The search for the presence of compounds of the coumarin type in the FGW and EtOH/Water extract from the *Aesculus hippocastanum* flower that were obtained in Example 1 is done by HPLC-UV-DAD, using a SymmetryShield 3.5 µm column (150×4.6 mm) and calibration molecule solutions of esculetin, esculin, fraxin and fraxetin. The interpretation is done by comparing the residence times and UV adsorption spectrums of the calibration molecules and the molecules present in the extract.

The search for the presence of compounds of the saponin type in the FGW and EtOH/Water extract from the *Aesculus hippocastanum* flower that were obtained in Example 1 is done by HPLC-UV-DAD, using a SymmetryShield 5 µm column (250×4.6 mm) and a calibration molecule solution of aescin. The interpretation is done by comparing the residence times and UV adsorption spectrums of the calibration molecule and the molecules present in the extract.

TABLE 2

| Result of the search for the presence of coumarins and saponins in the *Aesculus hippocastanum* flower extract | | |
|---|---|---|
| Solvent | FGW | EtOH/water |
| Part used | Flower | Flower |
| Saponins | absent | absent |
| Coumarins | absent | absent |

Conclusion:

Unlike *Aesculus hippocastanum* seed or bark extract, the FGW flower extract does not contain compounds of the saponin and coumarin types any more than the EtOH/water flower extract. This experiment shows that the chemical composition of the *Aesculus hippocastanum* extract does not depend on the choice of the extraction solvent alone, but also on the plant part used.

9

Example 4

Effect of an *Aesculus hippocastanum* FGW Flower Extract According to the Invention on the Protein Expression of Collagen IV in Normal Human Dermal Fibroblasts Protocol:

A fluoroimmunoassay test was carried out and consists of revealing the antigen of interest, in this case collagen IV. This method is semi-quantitative, highly sensitive and reproducible, and has the advantage of detecting the protein of interest in its native form in its environment, without any denaturation process. The fibroblasts, from a biopsy of the abdominal skin of donors between 30 and 60 years of age, are extracted and fixed to the bottom of a well at a density of 8,000 cells per well, and grow for 96 hours in a defined medium. The cells are next cultivated for 48 hours with the FGW flower extract obtained in example 1 tested at different concentrations or with the extraction solvent alone or without the extract, known as control. The cells are then washed in a phosphate-buffered saline (PBS) before being fixed, permeabilized and saturated with BSA (bovine serous albumen) at 1% for 30 minutes. The cells are incubated with the primary antibody (anti-collagen IV) for 1 hour, washed in PBS buffer, then incubated with the secondary antibody bonded to the Eu-N1 fluorochrome for 1 hour. The fluorescence is read on a spectrofluorimeter (Tecan M1000) with the appropriate filters. The fluorescence measurements are compared to the assayed quantity of DNA.

The results are provided in Table 3 below. The experiment is done 6 times (n=6). The values of the table represent the percentage values compared to the untreated control cells. The values represent the average of several experiments (n=6) on different extract lots. "Avg" refers to the average, and "SD" is the standard deviation.

TABLE 3

Percentage of protein expression of the collagen IV in normal human dermal fibroblasts as a function of the dose of *Aesculus hippocastanum* FGW flower extract used.

|  | Avg | EC |
| --- | --- | --- |
| Control | 100 | 10 |
| Extraction solvent at 0.5% (FGW) | 101.8 | 11.3 |
| *Aesculus hippocastanum* extract at 0.05% | 100.52 | 12.3 |
| *Aesculus hippocastanum* extract at 0.1% | 120.8 | 7.4 |
| *Aesculus hippocastanum* extract at 0.18% | 147.49 | 9.7 |
| *Aesculus hippocastanum* extract at 0.25% | 162.68 | 12.1 |
| *Aesculus hippocastanum* extract at 0.5% | 329.05 | 34.8 |

Conclusion:

The FGW flower extract obtained according to the invention causes a significant and dose-dependent increase of the protein expression of collagen IV. The extraction solvent alone does not cause an increase in the expression of collagen IV.

The FGW flower extract obtained according to the invention therefore causes an improvement in the protein synthesis of the macromolecular network of the dermal-epidermal junction.

10

Example 5

Effect of an FGW Flower Extract, an EtOH/Water Flower Extract and an FGW Seed Extract of *Aesculus hippocastanum* on the Protein Expression of Collagen IV in Normal Human Dermal Fibroblasts The protocol is identical to that of Example 4, with the exception that a comparative test is done of an EtOH/water flower and FGW seed extract obtained in Example 1 at a concentration of 0.25%.

The results are shown in the following table:

TABLE 4

Percentage of protein expression of the collagen IV in normal human dermal fibroblasts between FGW flower, EtOH/water flower, FGW seed extracts of *Aesculus hippocastanum*.

|  | Avg | SD |
| --- | --- | --- |
| Control | 100 | 4.96 |
| EtOH/Water extraction solvent at 0.25% | 93.87 | 8.39 |
| FGW extraction solvent at 0.25% | 93.96 | 13.56 |
| EtOH/water flower extract at 0.25% | 212.84 | 17.88 |
| FGW flower extract at 0.25% (invention) | 411.72 | 28.23 |
| FGW seed extract at 0.25% | 102.21 | 12.76 |

The FGW flower extract obtained according to the invention causes an increase of the protein expression of collagen IV about 2 times greater than the same extract obtained with an EtOH/Water solvent. The FGW seed extract does not cause an increase in the expression of collagen IV.

Example 6

Effect of an *Aesculus Hippocastanum* FGW Flower Extract According to the Invention on the Protein Expression of Collagen VII in Normal Human Fibroblasts Protocol:

The technique is the same as in Example 4, except that the antigen of interest is collagen VII. The results are provided in Table 4 below. The experiment is done 6 times (n=6). The values of the table represent the percentage values compared to the untreated control cells. The values represent the average of several experiments (n=6) on different extract lots. "Avg" refers to the average, and "SD" is the standard deviation.

TABLE 5

Percentage of protein expression of the collagen VII in normal human dermal fibroblasts as a function of the dose of *Aesculus hippocastanum* FGW flower extract used.

|  | Avg | SD |
| --- | --- | --- |
| Control | 100 | 15.9 |
| FGW extraction solvent at 0.5% | 93.6 | 6 |
| *Aesculus hippocastanum* extract at 0.05% | 110.2 | 6.4 |
| *Aesculus hippocastanum* extract at 0.1% | 130.1 | 13 |
| *Aesculus hippocastanum* extract at 0.18% | 159.5 | 13.2 |
| *Aesculus hippocastanum* extract at 0.25% | 144.7 | 12.5 |
| *Aesculus hippocastanum* extract at 0.5% | 151.5 | 16 |

Conclusion:

The FGW flower extract obtained according to the invention caused a significant and dose-dependent increase of the protein expression of collagen VII. The extraction solvent alone does not cause an increase in the expression of collagen VII. The FGW flower obtained according to the invention therefore causes an improvement in the protein synthesis of the macromolecular network of the dermal-epidermal junction.

Example 7

Effect of an FGW Flower Extract, an EtOH/Water Flower Extract and an FGW Seed Extract of *Aesculus hippocastanum* on the Protein Expression of Collagen VII in Normal Human Dermal Fibroblasts The protocol is identical to that of Example 6, with the exception that a comparative test is done of an EtOH/water flower and FGW seed extract obtained in Example 1 at a concentration of 0.25%.

The results are shown in the following table:

TABLE 6

Percentage of protein expression of the collagen VII in normal human dermal fibroblasts between FGW flower, EtOH/water flower, FGW seed extracts of *Aesculus hippocastanum*.

|  | Avg | SD |
| --- | --- | --- |
| Control | 100 | 4.96 |
| EtOH/Water extraction solvent at 0.25% | 100.11 | 12.99 |
| FGW extraction solvent at 0.25% | 103.82 | 13.15 |
| EtOH/water flower extract at 0.25% | 146.01 | 11.90 |
| FGW flower extract at 0.25% (invention) | 170.59 | 18.48 |
| FGW seed extract at 0.25% | 113.18 | 14.92 |

The FGW flower extract obtained according to the invention causes a greater increase of the protein expression of collagen VII compared to the same extract obtained with an EtOH/water solvent. The seed extract implementing the FGW solvent does not cause an increase in the expression of collagen VII.

Example 8

Effect of an *Aesculus hippocastanum* FGW Flower Extract According to the Invention on the Protein Expression of Fibronectin in Normal Human Dermal Fibroblasts Protocol:

The technique is the same as in Example 4, but with the following changes:
- the antigen of interest is fibronectin;
- the cells grow for 24 hours in a defined medium before being cultivated for 72 hours with the FGW flower extract obtained in Example 1;
- the secondary antibody is bonded to the Alexa 488 fluorochrome;
- The fluorescence is read on a high-resolution imaging system (INCELL Analyzer™1000), and the fluorescence measurements are quantified by image analysis (fluorescence area/number of cores with Hoechst staining). The results are provided in Table 5 below.

The experiment is done 3 times (n=3). The values of the table represent the percentage values compared to the untreated control cells. The values represent the average of several experiments (n=3) on different extract lots. "Avg" refers to the average, and "SD" is the standard deviation.

TABLE 7

Percentage of protein expression of fibronectin in normal human dermal fibroblasts treated with the *Aesculus hippocastanum* FGW flower extract at 0.5%.

|  | Avg | SD |
| --- | --- | --- |
| Control | 100 | 3.7 |
| *Aesculus hippocastanum* FGW flower extract at 0.5% | 117.3 | 2.7 |

Conclusion:

The FGW flower extract obtained according to the invention caused a significant increase in the protein expression of fibronectin in normal human dermal fibroblasts. The FGW flower obtained according to the invention therefore causes an improvement in the protein synthesis of the dermal matrix.

Example 9

Effect of an FGW Flower Extract and an FGW Seed Extract of *Aesculus hippocastanum* on the Protein Expression of Fibronectin in Normal Human Dermal Fibroblasts The protocol is identical to that of Example 8, with the exception that a comparative test is done of an FGW flower and FGW seed extract obtained in Example 1 at a concentration of 0.25%.

The results are shown in the following table:

TABLE 8

Percentage of protein expression of fibronectin in normal human dermal fibroblasts treated with the *Aesculus hippocastanum* FGW flower or FGW seed extract

|  | Avg | SD |
| --- | --- | --- |
| Control | 100 | 6.64 |
| FGW extraction solvent at 0.25% | 102.07 | 4.39 |
| FGW flower extract at 0.25% (invention) | 120.73 | 4.14 |
| FGW seed extract at 0.25% | 98.33 | 5.20 |

The FGW flower extract obtained according to the invention causes a significant increase in the protein expression of fibronectin in normal human dermal fibroblasts, while the FGW seed extract does not cause an increase in fibronectin expression.

Example 10

Effect of an *Aesculus hippocastanum* FGW Flower Extract According to the Invention on the Protein Expression of Collagen IV in Normal Human Keratinocytes Protocol:

The technique is the same as in Example 4, except that it is carried out on normal human keratinocytes and the antigen of interest is collagen IV. The results are provided in Table 6 below. The experiment is done 6 times (n=6). The values of the table represent the percentage values compared to the untreated control cells. The values represent the average of several experiments (n=6) on different extract lots. "Avg" refers to the average, and "SD" is the standard deviation.

TABLE 9

Percentage of protein expression of collagen IV in normal human keratinocytes as a function of the dose of *Aesculus hippocastanum* FGW flower extract used.

|  | Avg | SD |
| --- | --- | --- |
| Control | 100 | 12 |
| FGW extraction solvent at 0.5% | 84 | 4.5 |
| *Aesculus hippocastanum* extract at 0.05% | 117.7 | 5 |
| *Aesculus hippocastanum* extract at 0.1% | 158 | 19.7 |
| *Aesculus hippocastanum* extract at 0.18% | 173.9 | 11.9 |
| *Aesculus hippocastanum* extract at 0.25% | 257.4 | 26 |
| *Aesculus hippocastanum* extract at 0.5% | 349.2 | 53.3 |

Conclusion:

The FGW flower extract obtained according to the invention caused a significant and dose-dependent increase of the protein expression of collagen IV. The extraction solvent alone does not cause an increase in the expression of collagen IV. The FGW flower extract obtained according to the invention therefore causes an improvement in the protein synthesis of the macromolecular network of the dermal-epidermal junction.

Example 11

Effect of an FGW Flower Extract and an FGW Seed Extract of *Aesculus hippocastanum* on the Protein Expression of Collagen IV in Normal Human Keratinocytes The protocol is identical to that of Example 10, with the exception that a comparative test is done of an FGW flower and FGW seed extract obtained in Example 1 at a concentration of 0.25%.

The results are shown in the following table:

TABLE 10

Percentage of protein expression of collagen IV in normal human keratinocytes treated with the *Aesculus hippocastanum* FGW flower or FGW seed extract

|  | Avg | SD |
| --- | --- | --- |
| Control | 100 | 8.15 |
| FGW extraction solvent at 0.25% | 99.52 | 12.40 |
| FGW flower extract at 0.25% (invention) | 142.20 | 13.20 |
| FGW seed extract at 0.25% | 102.97 | 9.95 |

The FGW flower extract obtained according to the invention causes a significant increase in the protein expression of collagen IV in normal human keratinocytes, while the FGW seed extract does not cause an increase in collagen IV expression.

Example 12

Compositions Comprising the *Aesculus hippocastanum* Extract According to the Invention Day Cream

| Ingredient names | Composition (weight %) |
| --- | --- |
| DEMINERALIZED WATER | QS100 |
| CARBOPOL ULTREZ 21 | 0.10 |
| GLYCERIN | 3.00 |
| BUTYLENE GLYCOL | 5.00 |
| PENTYLENE GLYCOL | 2.00 |
| XANTHAN GUM | 0.20 |
| EMULIUM ® DELTA | 3.00 |
| PHENOXYETHANOL | 0.30 |
| SILICONE OIL | 4.00 |
| EXTRACT ACCORDING TO THE INVENTION | 2.00 |
| SODIUM HYDROXIDE (aqueous solution 10%) | 0.25 |
| Total | 100.00 |

Hydrating Natural Cream Gel

| Ingredient names | Composition (weight %) |
| --- | --- |
| EMULIUM ® MELLIFERA | 2.5 |
| NATURAL SQUALANE | 2.0 |
| DICAPRYLYL CARBONATE | 15.0 |
| DEMINERALIZED WATER | QS100 |
| GLYCERIN | 20.0 |
| TAPIOCA STARCH | 5.0 |
| EXTRACT ACCORDING TO THE INVENTION | 2.0 |
| ETHYLHEXYLGLYCERIN | 0.1 |
| PHENOXYETHANOL | 0.9 |
| FRAGRANCE | 0.2 |
| Total | 100.0 |

Nourishing Spray

| Ingredient names | Composition (weight %) |
| --- | --- |
| EMULIUM ® MELLIFERA | 2.00 |
| LABRAFAC ™ CC | 5.00 |
| LIPOCIRE ™ A | 3.00 |
| OCTYLDODECYL MYRISTATE | 5.00 |
| SILICONE OIL | 2.00 |
| DEMINERALIZED WATER | QS100 |
| STEAROYLE SODIUM GLUTAMATE | 0.50 |
| GLYCERIN | 5.00 |
| BUTYLENE GLYCOL | 5.00 |
| PEMULEN TR-2 | 0.10 |
| XANTHAN GUM | 0.15 |
| EXTRACT ACCORDING TO THE INVENTION | 2.00 |
| TEA STEARATE | 0.10 |
| PHENOXYETHANOL | 0.45 |
| ETHYLHEXYLGLYCERIN | 0.05 |
| FRAGRANCE | 0.05 |
| Total | 100.00 |

Water in Oil Emulsion

| Ingredient names | Composition (weight %) |
| --- | --- |
| PLUROL ® DIISOSTEARYL CG | 4.0 |
| HYDROGENATED RICIN OIL | 2.0 |
| COMPRITOL ® 888 CG | 1.0 |
| NATURAL SQUALANE | 3.0 |
| NATURAL ALKANE | 22.0 |
| MAGNESIUM SILICATE | 3.0 |
| DEMINERALIZED WATER | QS100 |
| GLYCERIN | 3.0 |
| MAGNESIUM SULFATE 7H$_2$O CODEX | 1.5 |
| SODIUM CHLORIDE CODEX | 1.5 |

-continued

| Ingredient names | Composition (weight %) |
|---|---|
| FRAGRANCE | 0.3 |
| EXTRACT ACCORDING TO THE INVENTION | 2.0 |
| PHENOXYETHANOL | 0.9 |
| ETHYLHEXYLGLYCERIN | 0.1 |
| Total | 100.0 |

What is claimed is:

1. A method of improving an appearance of a skin and/or a mucosa, to improve cutaneous strength and/or elasticity, to treat or prevent skin aging, wrinkles, or skin slackening, the method comprising:
   administering an extract for a cosmetic treatment of the skin and/or mucosa,
   said extract being an *Aesculus hippocastanum* extract obtained by an extraction method comprising:
   a solid/liquid extraction step of a flower of *Aesculus hippocastanum* with a solvent, followed by
   a second solid/liquid separation step, and
   a third step for recovering the liquid phase,
   wherein the solvent consists of a mixture of fructose and glycerin and water.

2. The method according to claim 1, wherein the extract has a flavonoid content level between 10 and 200 mg/100 g of extract.

3. The method according to claim 1, wherein the extract has a free amino acid content level between 10 and 200 mg/100 g of extract.

4. The method according to claim 1, to stimulate the synthesis of collagen IV, collagen VII and fibronectin.

5. The method according to claim 1, comprising administering a cosmetic composition comprising said extract.

6. The method according to claim 5, wherein the extract represents between 0.1% and 10% by weight of the composition.

* * * * *